United States Patent [19]
Tomomasa et al.

[11] Patent Number: 5,948,393
[45] Date of Patent: Sep. 7, 1999

[54] MAKE-UP COSMETIC COMPOSITION

[75] Inventors: Satoshi Tomomasa; Hirotaka Takada; Yoshikazu Soyama, all of Yokohama, Japan

[73] Assignee: Shiseido Company, Ltd., Tokyo, Japan

[21] Appl. No.: 08/872,459

[22] Filed: Jun. 11, 1997

Related U.S. Application Data

[63] Continuation of application No. 08/483,630, Jun. 7, 1997, abandoned, which is a continuation of application No. 08/159,983, Nov. 30, 1993, abandoned.

[30] Foreign Application Priority Data

Nov. 30, 1992 [JP] Japan .................................... 4-343508
Nov. 12, 1993 [JP] Japan .................................... 5-307222

[51] Int. Cl.$^6$ ........................................................ A61K 7/021
[52] U.S. Cl. ............................................................ 424/63
[58] Field of Search ................................................. 424/63

[56] References Cited

U.S. PATENT DOCUMENTS

| | | | |
|---|---|---|---|
| 4,536,405 | 8/1985 | Nara et al. | 424/63 |
| 4,980,155 | 12/1990 | Shah et al. | 424/63 |
| 5,036,108 | 7/1991 | Asahi et al. | 424/63 |
| 5,053,220 | 10/1991 | Arraudeau et al. | 424/63 |
| 5,053,221 | 10/1991 | Robertson et al. | 424/63 |
| 5,108,736 | 4/1992 | Schlossman | 424/63 |
| 5,389,363 | 2/1995 | Snyder et al. | 424/63 |

FOREIGN PATENT DOCUMENTS

| | | |
|---|---|---|
| 0374332 | 6/1990 | European Pat. Off. . |
| 2229393 | 12/1974 | France . |
| 52-27695 | 7/1977 | Japan ..................................... 424/63 |

OTHER PUBLICATIONS

Patent Abstracts of Japan, vol. 10, No. 362, abstract of JP 61–158913, (1986).
Patent Abstracts of Japan, vol. 14, No. 431, abstract of JP 02–167212, (1990).

*Primary Examiner*—Peter F. Kulkosky
*Attorney, Agent, or Firm*—Sprung Kramer Schaefer & Briscoe

[57] ABSTRACT

A water-in-oil type make-up cosmetic composition having excellent water resistance, perspiration resistance, sebum resistance, and oil resistance and containing 1 to 54% by weight of an oil-soluble resin in an external phase and 0.0001 to 63% by weight of a coloring material in an internal phase.

8 Claims, No Drawings

MAKE-UP COSMETIC COMPOSITION

This application is a continuation of application Ser. No. 08/483,630, filed on Jun. 7, 1997, now abandoned which is a continuation of application Ser. No. 08/159,983, filed on Nov. 30, 1993, now abandoned.

TECHNICAL FIELD

The present invention relates to a make-up cosmetic composition, more specifically to a make-up cosmetic composition such as a mascara, an eyeliner, a foundation, or a spot cover superior in water resistance, perspiration resistance, sebum resistance, and oil resistance (i.e., against oil components contained in foundations, creams, cosmetic bases, and other cosmetics) and superior in cosmetic staying power.

BACKGROUND ART

As mascaras, eyeliners, and other make-up cosmetics, there have conventionally been known, roughly devided, emulsion types, film types, emulsion-film types, oil types, oil-emulsion types, and oil-film types. A brief explanation will be given of these various types below.

First, the emulsion type is an oil-in-water type emulsion comprised mainly of a solid, semi-solid, or liquid oil and an aqueous system. Cosmetics of this type easily are detached due to water, perspiration, tears, etc. Further, mascara etc. runs into the sebum on the face and the oil components of the emulsion or other cosmetics and thus tends to stain the area around the eyes with lapse of time.

Next, regarding the film type, use has been made of polymer emulsions obtained by emulsion polymerization using natural latex or water-soluble polymers or emulsifiers as the film forming agent, but these polymer materials themselves are poor in water resistance, and therefore, could not give sufficient water resistance as a cosmetic.

An attempt was made to solve these problems with a solid, semi-solid oil—water—polymer emulsion type emulsion-film type of cosmetic as disclosed in Japanese Unexamined Patent Publication (Kokai) No. 50-125043. However, while it was possible to delay the penetration of water by formulating wax thereto, no consideration was given to the water resistance of the polymer emulsion per se so that the solution was not necessarily complete.

The oil type is comprised of a solid, semi-solid, or liquid oil component—volatile branched hydrocarbon system, so is excellent in water resistance, but is completely poor in oil resistance and dryness.

The oil-emulsion type is a solid, semi-solid, or liquid oil component—volatile branched hydrocarbon—aqueous water-in-oil type emulsion. This is excellent in water resistance and dryness, but in general the composition is obtained by dissolving solid paraffin, wax, or a lanolin derivative in a volatile branched hydrocarbon, then dispersing various types of pigment powders therein, so especially in the case of mascaras and eyeliners, even after drying, the mascara or eyeliner dissolves into the sebum or oil component of other cosmetics present there due to blinking etc., so the pigment falls off from the film and adheres to the lower eyelids (secondary adhesion) or stains the area around the eyes, that is, the oil resistance is poor.

An attempt was made to solve this problem by the oil-film type obtained by mixing an oil-soluble film agent as disclosed in Japanese Unexamined Patent Publication (Kokai) No. 52-27695. This is an oil-in-water-in-oil type (O/W/O) comprised of a solid, semi-solid, liquid oil component—volatile branched hydrocarbon—synthetic resin emulsion system. Since both the oil and water are used as volatile solvents and each include solid components and film agents, the cosmetic staying power is improved. Since the pigments are included in the external phase, however, the pigments redisperse due to the sebum and the oil component contained in the cosmetics, so it is not possible to prevent detachment or to completely eliminate adhesion or running, as disclosed in, for example, JP-A-58-180412.

Recently, further, the technology for a make-up cosmetic using an organic silicone resin as a film agent has been developed (Japanese Unexamined Patent Publication (Kokai) Nos. 61-18708, 61-65809, and 61-161211). The following characteristics are obtained when an organic silicone resin is used, so this is useful:

(1) A strong film is formed after drying.
(2) After drying, there is complete insolubility in the water or film component, cream, emulsion, cosmetic base, or other oil components used in cosmetics.
(3) There is, however, solubility in the volatile oil component used in make-up removers etc.

In the above inventions, however, since an organic silicone resin is formulated in the same phase as the phase in which the pigment or solid, semisolid, or liquid oil component, oil-soluble resin, etc. are dispersed or dissolved, after drying, the organic silicone resin becomes a discontinuous film due to the pigment. Accordingly, the film swells due to the liquid oil component and physical stimulus causes detachment or running of the pigment. The above was the prior art for make-up cosmetics such as eyeliners and mascaras.

In addition, one technology for improving the cosmetic staying power of make-up cosmetics was a hydrophobic treatment with powder. The main type of this was treatment with silicone which is superior in water repellency and oil repellency (see U.S. Pat. No. 4988502, Japanese Examined Patent Publication (Kokoku) No. 41-9890, Japanese Examined Patent Publication (Kokoku) No. 45-2915, Japanese Examined Patent Publication (Kokoku) No. 45-18999, Japanese Unexamined Patent Publication (Kokai) No. 54-56083, Japanese Unexamined Patent Publication (Kokai) No. 61-189211, and Japanese Examined Patent Publication (Kokoku) No. 2-191211). The development of these silicone treatment powders has, in particular, improved the cosmetic staying power of foundations, spot covers, etc., but since the pigment per se is exposed to the external environment, while there is the effect of shedding water, the cosmetic washes away with a large amount of water or oil or easily comes off with physical friction to thus stain the collars of shirts.

Accordingly, the object of the present invention is to provide a water-in-oil type make-up cosmetic composition which is superior in water resistance, perspiration resistance, sebum resistance, and oil resistance.

In accordance with the present invention, there is provided a water-in-oil type make-up cosmetic composition which includes 1 to 54% by weight of an oil-soluble resin in an external phase and includes a coloring material in an inner phase.

The present inventors engaged in intensive studies in consideration of these circumstances and as a result completed the make-up cosmetic of the present invention, which (1) can guard against the pigment directly contacting the external environment by mixing the pigment or other coloring agent into the inner phase and (2) can maintain continuity of the film after drying by mixing an oil-soluble resin, in particular, an organic silicone resin, in the external phase, whereby the cosmetic staying power can be strikingly improved, there is no running at all into water or oil, and the cosmetic can be removed by quickly dissolving in a volatile oil component of a remover or the like.

The constitution of the present invention will be explained in detail below.

First, the oil phase of the water-in-oil type makeup cosmetic composition of the present invention is mainly composed of an oil-soluble resin and a volatile oil component.

As the oil-soluble resin used in the present invention, mention may be made of fluoro resins, silicone resins, aromatic hydrocarbon resins, terpene resins, polybutene, polyisoprene, alkyd resins, and PVP modified polymers.

The fluoro resins include acrylic resins containing perfluoroalkyl groups, methacrylic resins containing perfluoroalkyl groups, and other resins having perfluoroalkyl groups as a pendant group in the main chain of a hydrocarbon, resins where the main chain per se is a fluorocarbon, such as polyfluorovinylidene, and resins having both a hydrocarbon portion and a fluorocarbon portion at the main chain obtained by radical copolymerization of fluoroethylene and a hydrocarbon type vinyl ether, but the resins are not limited to the above-mentioned compounds so long as the resins dissolve in a volatile solvent. For example, mention may be made of Fluorocoat EC-104, Fluorocoat EC-106, Fluorocoat EC-200, Fluorocoat EC-300 (made by Asahi Glass Co., Ltd.) etc. which are available on the market in a form dissolved in a volatile solvent.

The silicone resin is a copolymer composed of structural units of $SiO_2$, $RSiO_{3/2}$, $R_2SiO$, or other units of the general formula $R_nSiO_{4-n/2}$ (wherein, R is a hydrogen atom, a hydrocarbon group having 1 to 6 carbon atoms, or a phenyl group, and n is a number of 1.0 to 1.8) or copolymers obtained by terminating the end with $R_3SiO_{1/2}$ (wherein R is the same as mentioned above). More specifically, mention may be made of KR-285, KR-278, KR-114, etc. of Shin-Etsu Chemical Co., Ltd. Use may be made of silicone rubber of a polymerization degree n of dimethylpoly-siloxane of 5000 to 8000.

Further, as the aromatic hydrocarbon resin, mention may be made of Nisseki Neopolymer T, 120, 140, etc. of Nihon Sekiyu Co., Ltd. As a terpene resin, mention may be made of Quintone A-100, B-170, C-100, etc. of Nippon Zeon Co., Ltd. As the polybutene, mention may be made of Polybutene 200 etc. of Idemitsu Sekiyu Co., Ltd. As the polyisoprene, mention may be made of EscoRez 1071, 1103, etc. of Exxon Corp. As the alkyd resin, mention may be made of Veccozol EL8011, Solid Veccozol No. 31, No. 96, etc. of Dainippon Ink and Chemicals Co., Ltd. As the PVP modified polymer, mention may be made of Ganex V-216, V-220, etc. of Gokyo Sangyosha Co., Ltd.

Among these resins, when use is made of an organic silicone resin, a particularly good film can be obtained. This is preferable in terms of the water resistance, perspiration resistance, oil resistance, etc.

Among the organic silicone resins, particularly preferred is an organic silicone resin composed of the general formula $R_3SiO_{1/2}$ units (wherein R is a hydrocarbon group having 1 to 6 carbon atoms or a phenyl group) and $SiO_2$ units present in a range of a ratio of the $R_3SiO_{1/2}$ units to $SiO_2$ units of 0.5/1 to 1.5/1.

These resins are included in an amount of 2 to 60% by weight based on the total weight of the oil phase, preferably 2 to 50% by weight from the viewpoint of usability (i.e., smoothness of application), more preferably 5 to 50% by weight in view of the water resistance and oil resistance.

In the oil phase of the cosmetic composition according to the present invention, in addition to the above-mentioned oil-soluble resin, 40 to 98% by weight of a volatile oil component may be preferably formulated thereto. The volatile oil component in the oil phase may be a solvent for the resin. It is a hydrocarbon oil or silicone oil with a boiling point, at room temperature, of 60 to 260° C. For example, mention may be made of Isopar (registered trademark) A, C, D, E, G, H, K, L, and M (Exxon Corp.), Sortrol (registered trademark) 100, 130, and 220 (Philips Corp.), and organic silicone oils expressed by the following general formulas (I) and (II):

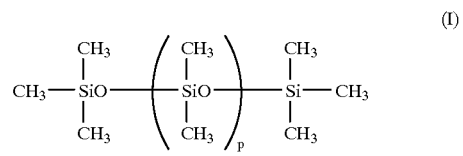

(wherein, p is an integer of from 0 to 3)

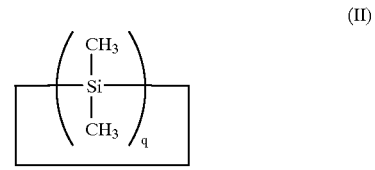

(wherein q is an integer of from 4 to 6).

The amount of the total oil phase formulated is preferably 20 to 95% by weight, based on the total weight of the make-up cosmetic, more preferably 40 to 98% by weight.

The oil phase may further contain therein, in accordance with other objectives, within a range of amounts or quality not impairing the effect of the present invention, components generally used for cosmetics, such as solid, semisolid, or liquid oil components, pharmaceuticals, emulsifiers, thickeners, UV absorbers, clay minerals, perfumes, or other volatile components.

Next, an explanation will be made of the aqueous phase of the make-up cosmetic composition according to the present invention.

The coloring material contained in the aqueous phase may be any coloring material conventionally used for make-up cosmetics. For example, mention may be made of talc, mica, kaolin, calcium carbonate, zinc oxide, titanium dioxide, red iron oxide, yellow iron oxide, black iron oxide, ultramarine, navy blue, carbon black, lower titanium oxide, cobalt violet, chromium oxide, chromium hydroxide, cobalt titanate, bismuth oxychloride, titanium mica type pearl pigments, and other inorganic pigments, Red 201, Red 202, Red 204, Red 205, Red 220, Red 226, Red 228, Red 405, Orange 203, Yellow 205, Yellow 4, Yellow 5, Blue 1, Blue 404, Green 3, and other zirconium, barium, or aluminum lakes or other organic pigments, chlorophyll, β-carotene, and other natural colors, nylon, cellulose, polyethylene, and other resin powders, dyes, etc.

Note that, for the purpose of improving the running resistance, it is preferable to use a hydrophilic coloring material so that the coloring material does not travel to the external phase, but the present invention is not limited to this, i.e., even an oleophilic coloring material may be used so long as the surface of the coloring material is made hydrophilic by a hydrophilic treatment or surfactant.

The content of these coloring materials is 0.0001 to 63% by weight in the water phase, preferably 0.1 to 50% by weight, and preferably 0.001 to 50% by weight, based upon the total weight of the make-up cosmetic composition, more preferably 0.1 to 40% by weight.

In the aqueous phase, there may preferably be mixed an emulsion resin having a film-forming ability from the viewpoint of additional usability (i.e., adhesion of film). The amount of mixture at that time is preferably 0.1 to 80% by weight of the water phase.

As the emulsion resin, mention may be made of the emulsion resins described in British Patent No. 1110240, U.S. Pat. No. 3639572, Japanese Unexamined Patent Publication (Kokai) No. 48-36347, Japanese Unexamined Patent Publication (Kokai) No. 1-203313, etc., that is, ethyl acrylate, methyl methacrylate, butyl methacrylate, methacrylic acid, vinylidene chloride and vinyl chloride copolymer emulsions, etc.

The amount of the total aqueous phase formulated is preferably 5 to 80% by weight, based upon the total weight of the make-up cosmetic composition, more preferably 20 to 60% by weight.

The water phase may also contain, in accordance with other objectives, within a range of amounts or quality not impairing the effect of the present invention, preservatives, alcohol, polyhydric alcohol, pharmaceuticals, surfactants, water-soluble polymers, thickeners, clay minerals, perfumes, antioxidants, UV absorbers, moisture retainers, etc.

EXAMPLES

The present invention will now be explained in further detail by the following Examples. The present invention is not limited to these Examples. The amounts formulated (%) shown are percents by weight. Before the Examples, an explanation will be made of the methods of testing the effects and the methods of evaluation of the present invention.

Comparative Example 1: Oil-Solvent Type Eyeliner

|  | % |
|---|---|
| Wax: | |
| Carnauba wax | 4.0 |
| Beeswax | 2.0 |
| Microcrystalline wax | 9.0 |
| White vaseline | 2.0 |
| Solvent: | |
| Liquid polyisobutylene | 72.5 |
| Gelation agent: | |
| Organic bentonite | 0.5 |
| Pigment: | |
| Titanium dioxide | 8.0 |
| Carbon black | 2.0 |
| Additives: | |
| Preservative | q.s. |

Production method: Organic bentonite was added to a portion of the liquid polybutylene. The mixture was passed through a colloid mill to disperse the bentonite therein, then was gelled. Next, the waxes and preservative were mixed. The mixture was heated to dissolve them, then the pigments were added. The mixture was then cooled and kneaded by a roll mill, then was again heated to dissolve. Into this were added the bentonite gel and the remaining portion of the liquid polyisobutylene. The mixture was cooled, while stirring.

Comparative Example 2: Aqueous Eyeliner

|  | % |
|---|---|
| Polyacrylic acid emulsion resin (50% liquid) | 30.0 |
| 3% bentonite liquid dispersion | 15.0 |
| Butylene glycol | 5.0 |
| Precipitated calcium carbonate | 5.0 |
| Pigment | 20.0 |
| Purified water | 25.0 |
| Perfume | q.s. |

A 3% bentonite liquid dispersion was prepared. To this were successively added butylene glycol, purified water, precipitated calcium carbonate, the pigment, the preservative, and the perfume, then the mixture was passed through a colloid mill. Next, the polyacrylic acid emulsion resin was added and the mixture was stirred to make it homogeneous.

Comparative Example 3: Oil Mascara

|  | % |
|---|---|
| Carnauba wax | 7.0 |
| Beeswax | 2.0 |
| Microcrystalline wax | 20.0 |
| Lanolin | 0.4 |
| Liquid polyisobutylene | 57.6 |
| Organic modified bentonite | 3.0 |
| Pigment | 10.0 |
| Preservative | q.s. |

Production method: The same procedure was followed as in the case of the oil-solvent type eyeliner.

Comparative Example 4: Aqueous Mascara

|  |  | % |
|---|---|---|
| A: | Bentonite | 2.0 |
|  | Sodium carboxymethylcellulose (low viscosity) | 0.2 |
|  | Purified water | 10.0 |
| B: | Sodium laurate | 0.1 |
|  | Butylene glycol | 1.5 |
|  | Purified water | 38.3 |
| C: | Beeswax | 6.5 |
|  | Liquid paraffin | 3.5 |
|  | Carbon black | 1.5 |
| D: | Stearic acid | 1.0 |
|  | Carnauba wax | 5.0 |
| E: | Morpholine | 0.4 |
| F: | Vinyl acetate emulsion | 30.0 |
|  | Preservative | q.s. |

Production method:
(1) The bentonite and the sodium carboxymethyl cellulose were mixed together in a dry state, then heated purified water was added to swell and make the mixture homogeneous.

(2) To this was added B, then the mixture was heated to 65 to 70° C.

(3) D was added to C, then the mixture was heated to melt the same. This was cooled and then kneaded by a hot roll mill, then remelted and heated to 70° C.

(4) E was added to the mixture of A and B, then the mixture of C and D was added to emulsify the mixture. This was cooled while stirring to make the finished product.

Comparative Example 5: O/W/O Type Mascara (see Japanese Unexamined Patent Publication (Kokai) No. 52-27695

|  | % |
|---|---|
| (Oil phase) | |
| Isopar | 30 |
| Solid paraffin wax | 8 |
| Lanolin derivative | 8 |
| Sorbitan monopalmitate | 4 |
| Black iron oxide | 10 |
| (Aqueous phase) | |
| Polyacrylic acid ester emulsion | 30 |
| Ion exchanged water | 10 |
| Preservative | q.s. |
| Perfume | q.s. |

Production method: The oil phase portion was heated to 70° C. and stirred to make it homogeneous. The aqueous phase portion was heated to 70° C. and added to the oil phase portion to emulsify it. The mixture was then cooled and filled in mascara containers.

Comparative Example 6: Oil Foundation

|  | % |
|---|---|
| Substrate: | |
| Liquid paraffin | 18.0 |
| Isopropyl myristate | 15.0 |
| Liquid lanolin | 4.5 |
| Microcrystalline wax | 4.5 |
| Ceresine | 10.0 |
| Carnauba wax | 2.0 |
| Sorbitan sesquioleate | 1.0 |
| Antioxidant/preservative | q.s. |
| Pigment: | |
| Hydrophobically treated titanium dioxide | 15.0 |
| Hydrophobically treated kaolin | 20.0 |
| Hydrophobically treated mica | 10.0 |
| Hydrophobically treated coloring pigment | q.s. |
| Perfume: | |
| Perfume | q.s. |

Production method: The pigments were mixed. The substrate components were mixed separately and heated to 70 to 80° C. to melt. The pigments were added to the melted substrate. The mixture was kneaded by a roll mill. The kneaded mixture was heated to melt, adjusted in color, then was cleared of bubbles, given perfume, and poured into a mold or container and cooled to form the final product.

Comparative Example 7: O/W Emulsion Foundation

|  | % |
|---|---|
| Oil phase: | |
| Stearic acid | 5.0 |
| Oleophilic glycerine monostearate | 2.5 |
| Cetostearyl alcohol | 1.0 |
| Propylene glycol monolaurate | 3.0 |
| Liquid paraffin | 7.0 |
| Isopropyl myristate | 8.0 |
| Butyl paraoxybenzoate | q.s. |
| Aqueous phase: | |
| Purified water | 52.3 |
| Triethanolamine | 1.2 |
| Sorbitol | 4.0 |
| Methyl paraoxybenzoate | q.s. |
| Pigments: | |
| Titanium dioxide | 8.0 |
| Kaolin | 5.0 |
| Talc | 2.0 |
| Bentonite | 1.0 |
| Coloring pigment | q.s. |
| Perfume: | |
| Perfume | q.s. |

Production method: The pigments were mixed and pulverized. The aqueous phase was prepared, then the mixed pigments were added to it and dispersed. The mixture was then heated to 75° C. The oil phase was prepared and then heated to 80° C. The oil phase was added to the aqueous phase, while stirring to make an emulsion, then this was cooled while stirring. Perfume was added at 50° C., then the mixture was further stirred and cooled to room temperature.

Comparative Example 8: W/O Type Emulsion Foundation

|  | % |
|---|---|
| Oil phase: | |
| Decamethyl cyclopentasiloxane | 20.0 |
| Perfume | q.s. |
| Oleophilic surfactant: | |
| Polyoxyalkylene modified organopolysiloxane | 5.0 |
| Pigment: | |
| Dextrin fatty acid ester treated pigment | 20.0 |
| Aqueous phase: | |
| Ion exchanged water | Balance |
| 95% Ethyl alcohol | 15.0 |
| 1,3-Butylene glycol | 3.0 |
| Mehtyl parabene | 0.1 |
| Sodium citrate | 0.05 |
| Sodium chondroitin sulfate | 0.05 |

The oil phase and the oleophilic surfactant were heated to 70° C. and mixed, then powder was added. The aqueous phase, which had been preheated to 70° C., was then added, emulsified, and dispersed. After this, the mixture was stirred and cooled to room temperature to obtain the desired emulsion foundation. The dextrin fatty acid ester treated pigment used here was obtained in accordance with the method described in Japanese Unexamined Patent Publication (Kokai) No. 62-205165, i.e., a mixture of mica, titanium dioxide, and iron oxide was adjusted to skin color, then added to a solution of dextrin fatty acid ester in Isopar E (registered trademark) (Exxon Chemical), this mixture was stirred, then the solvent was removed and the result was dried and pulverized. The dextrin fatty acid ester treated pigment was obtained by a similar method.

Examples 1 to 11

Eyeliners, mascaras, and foundations were obtained by the formulae described in Tables 1 to 3.

TABLE 1

|  | Ex. 1: Eyeliner | Ex. 2: Mascara | Ex. 3: Foundation |
|---|---|---|---|
| Aqueous phase |  |  |  |
| Coloring pigment |  |  |  |
| Iron oxide black | 10 | 5 | — |
| Titanium dioxide | — | — | 5 |
| Coloring pigment | — | — | 10 |
| Purified water | 26 | 31 | 31 |
| Vinyl acetate emulsion | 10 | 10 | — |
| Preservative | q.s. | q.s. | q.s. |
| Swelling clay mineral | 1 | 1 | 1 |
| Propylene glycol | 3 | 3 | 3 |
| Oil phase |  |  |  |
| Isopar E | 38 | 25 | 40 |
| Organic modified clay mineral | — | 3 | 3 |
| Organic silicone resin* | 10 | 20 | 5 |
| Sorbitan monopalmitate | 2 | 2 | — |
| Propylene glycol monolaurate | — | — | 2 |
| Perfume | q.s. | q.s. | q.s. |

*$(CH_3)_3SiO_{1/2}:SiO_2 = 1.5/1$

TABLE 2

|  | Ex. 4: Spot cover | Ex. 5 Base | Ex. 6: Mascara | Ex. 7: Mascara |
|---|---|---|---|---|
| Aqueous phase |  |  |  |  |
| Coloring pigment |  |  |  |  |
| Iron oxide black | — | — | 2 | 10 |
| Titanium dioxide | 10 | 10 | — | — |
| Coloring pigment | 10 | 10 | — | — |
| Purified water | 19.5 | 24 | 2.5 | 26 |
| Vinyl acetate emulsion | 10 | 10 | 1 | 15 |
| Preservative | q.s. | q.s. | q.s. | q.s. |
| Swelling clay mineral | 0.5 | 1 | — | 1 |
| Propylene glycol | 5 | 5 | 0.5 | 3 |
| Oil phase |  |  |  |  |
| Octamethyltetracyclosiloxane | 10 | 15 | 32 | 36 |
| Organic modified clay mineral | 3 | 5 | 6 | 5 |
| Organic silicone resin* | 30 | 18 | 54 | 2 |
| Sorbitan monopalmitate | — | 2 | 2 | 2 |
| Propylene glycol monolaurate | 0 | — | — | — |
| POE (2) lauryl ether | 2 | — | — | — |
| Perfume | q.s. | q.s. | q.s. | q.s. |

*$(CH_3)_3SiO_{1/2}:SiO_2 = 1/1$

TABLE 3

|  | Ex. 8: Eyeliner | Ex. 9: Mascara | Ex. 10: Foundation | Ex. 11: Foundation |
|---|---|---|---|---|
| Aqueous phase |  |  |  |  |
| Coloring pigment |  |  |  |  |
| Iron oxide black | 10 | 5 | — | — |
| Titanium dioxide | — | — | 5 | 5 |
| Coloring pigment | — | — | 15 | 15 |
| Purified water | 26.5 | 24 | 28 | 28 |
| Vinyl acetate emulsion | 10 | 15 | — | — |
| Preservative | q.s. | q.s. | q.s. | q.s. |
| Swelling clay mineral | 0.5 | 3 | 1 | 1 |
| Propylene glycol | 3 | 3 | 3 | 3 |
| Oil phase |  |  |  |  |
| Isopar E | 38 | 25 | 38 | 33 |
| Organic modified clay mineral | — | 3 | 3 | 3 |
| Polyisoprene resin | 10 | 20 | — | — |
| Aromatic hydrocarbon resin | — | — | 5 | 5 |
| Organic silicone resin* | — | — | — | 5 |
| Sorbitan monopalmitate | 2 | 2 | — | — |
| Propylene glycol monolaurate | — | — | 2 | 2 |
| Perfume | q.s. | q.s. | q.s. | q.s. |

*$(CH_3)_3SiO_{1/2}:SiO_2 = 1.5/1$

Example 12: Eyeliner

|  | % |
|---|---|
| (Aqueous phase) |  |
| Iron oxide black | 5 |
| Purified water | 19 |
| Polyacrylic acid emulsion | 20 |
| Preservative | q.s. |
| Swelling clay mineral | 1 |
| 1,3-Butanediol | 5 |
| (Oil phase) |  |
| Decamethylcyclopentasiloxane | 25 |
| Polyoxyalkylene modified organosiloxane (polyoxyalkylene group 20%) | 5 |
| Organic modified clay mineral | 5 |
| Perfume | q.s. |
| Organic silicone resin $(CH_3)_3SiO_{1/2}:SiO_2 = 1.8/1$ | 15 |

Examples 13 and 14: Mascara

|  | Ex. 13 (mascara) % | Ex. 14 (mascara) % |
|---|---|---|
| (Aqueous phase) |  |  |
| Coloring pigment |  |  |
| Iron oxide black | 2 | 10 |
| Titanium dioxide | — | — |
| Coloring pigment | — | — |
| Purified water | 2.5 | 26.5 |
| Vinyl acetate emulsion | 1 | 15 |
| Preservative | q.s. | q.s. |
| Swelling clay mineral | — | 0.5 |
| Propylene glycol | 0.5 | 3 |
| (Oil phase) |  |  |
| Isopar E | 32 | 36 |
| Organic modified clay mineral | 6 | 5 |
| Polyisoprene resin | 54 | 2 |

-continued

|  | Ex. 13 (mascara) % | Ex. 14 (mascara) % |
| --- | --- | --- |
| Sorbitan monopalmitate | 2 | 2 |
| Propylene glycol monolaurate | — | — |
| POE (2) lauryl ether | — | — |
| Perfume | q.s. | q.s. |

Method of Preparation (Examples 1 to 14)

The aqueous phase was added, while stirring, to the oil phase at room temperature and emulsified by a dispar.

The cosmetics of Examples 1 to 14 and of Comparative Examples 1 to 8 were tested as to the cosmetic staying power by the following methods of evaluation.

<Methods of Evaluation>

Contact Angle With Water

The samples were coated to a constant thicknesses (0.8 mm) on plates and allowed to dry a day and night, then water was dropped on them. The contact angle with the water was measured after 20 minutes. The larger the contact angle, the higher the water repellency and the better the water resistance.

Oil Resistance Test

The samples were coated to a constant thicknesses (0.8 mm) on acrylic plates of 5 mm×3 cm. These were immersed in a foundation oil component (liquid paraffin; isostearic acid=1:1) and allowed to stand for 25° C. The next day, the states of the film components were evaluated.

⊚: Film remained completely intact.

○: ⅓ or more of film remained.

Δ: ½ or more of film remained.

x: Only less than ½ of film remained.

The samples were tested and evaluated by actual usage tests by an expert panel of 20 subjects for each of the following items:

Perspiration Resistance and Sebum Resistance

The samples were applied and the subjects were made to play tennis for two hours on a sunny day to cause them to sufficiently perspire, then the states of the samples were judged visually.

⊚: 16 or more subjects responded there was no running.

○: 9 to 15 subjects responded there was no running.

Δ: 5 to 8 subjects responded there was no running.

x: 4 or less subjects responded there was no running.

Water Resistance

The samples were applied and the subjects were made to take showers for 2 minutes, then the states of the samples were judged visually.

⊚: 16 or more subjects responded there was no running.

○: 9 to 15 subjects responded there was no running.

Δ: 5 to 8 subjects responded there was no running.

x: 4 or less subjects responded there was no running.

Oil Resistance

The samples were applied and the subjects were made to play tennis for two hours on a sunny day to cause them to sufficiently perspire, then a visual judgement was made as to the existence of secondary adhesion to the lower eyelids in the case of mascara and eyeliner and of ruined make-up in the case of foundations and base cosmetics.

⊚: 16 or more subjects responded there was no secondary adhesion or ruined make-up.

○: 9 to 15 subjects responded there was no secondary adhesion or ruined make-up.

Δ: 5 to 8 subjects responded there was no secondary adhesion or ruined make-up.

x: 4 or less subjects responded there was no secondary adhesion or ruined make-up.

Applicability

The ease of application (smoothness of application) when applying the samples, the ease of drying, the homogenity of the finish, etc. were comprehensively evaluated.

○: 12 or more subjects responded the cosmetic was good.

Δ: 6 to 11 subjects responded the cosmetic was good.

x: 5 or less subjects responded the cosmetic was good.

The results are shown in Table 4 and Table 5.

TABLE 4

|  | Comparative Examples | | | | | | | |
| --- | --- | --- | --- | --- | --- | --- | --- | --- |
|  | 1 | 2 | 3 | 4 | 5 | 6 | 7 | 8 |
| Contact angle with water (°) | 92 | 2 | 115 | 12 | 112 | 92 | 5 | 82 |
| Oil resistance test | X | Δ | X | Δ | Δ | X | X | X |
| Perspiration resistance and sebum resistance | Δ | X | Δ | X | ○ | ○ | Δ | ○ |
| Water resistance | ○ | X | ○ | X | Δ | Δ | X | Δ |
| Oil resistance | Δ | X | Δ | X | ○ | ○ | Δ | X |
| Applicability | ○ | ○ | ○ | ○ | ○ | ○ | ○ | ○ |

TABLE 5

|  | Examples | | | | | | | | | | | | | |
| --- | --- | --- | --- | --- | --- | --- | --- | --- | --- | --- | --- | --- | --- | --- |
|  | 1 | 2 | 3 | 4 | 5 | 6 | 7 | 8 | 9 | 10 | 11 | 12 | 13 | 14 |
| Contact angle with water (°) | 111 | 112 | 106 | 110 | 101 | 112 | 101 | 107 | 108 | 110 | 110 | 102 | 110 | 100 |
| Oil resistance test | ⊚ | ⊚ | ⊚ | ⊚ | ⊚ | ⊚ | ○ | ○ | ○ | ○ | ⊚ | ⊚ | ○ | ○ |
| Perspiration resistance and sebum resistance | ⊚ | ⊚ | ⊚ | ⊚ | ⊚ | ⊚ | ⊚ | ○ | ○ | ○ | ⊚ | ⊚ | ⊚ | ⊚ |
| Water resistance | ⊚ | ⊚ | ⊚ | ⊚ | ⊚ | ⊚ | ⊚ | ⊚ | ⊚ | ⊚ | ⊚ | ⊚ | ⊚ | ⊚ |
| Oil resistance | ⊚ | ⊚ | ⊚ | ⊚ | ⊚ | ⊚ | ○ | ○ | ○ | ○ | ○ | ⊚ | ○ | ○ |
| Applicability | ○ | ○ | ○ | Δ | ○ | Δ | ○ | ○ | ○ | ○ | ○ | ○ | Δ | ○ |

As explained above, the make-up cosmetic of the present invention maintains continuity of the film of the external phase and the pigment is present in the internal phase, so there is no contact with the external environment and as a result the make-up cosmetic is extremely excellent in cosmetic staying power (water resistance, perspiration resistance, sebum resistance, oil resistance) and further does not run into other cosmetics (oil resistance).

We claim:

1. A water-in-oil type make-up cosmetic composition comprising (i) 20 to 95% by weight of an external oil phase containing 2 to 60% by weight of at least one oil-soluble resin selected from the group consisting of fluoro resins, silicone resins, aromatic hydrocarbon resins, terpene resins, polybutene, polyisoprene, alkyd resins and PVP modified polymers and 40 to 98% by weight of at least one volatile oil component selected from the group consisting of hydrocarbon oils and silicone oils, both based upon the total weight of the external oil phase, and (ii) 5 to 80% by weight of an inner aqueous phase containing 0.0001 to 63% by weight, based upon the total amount of the inner aqueous phase, of a coloring material which is hydrophilic or has a hydrophilic surface, said cosmetic composition exhibiting improved oil resistance in an oil resistance test.

2. A water-in-oil type make-up cosmetic composition as claimed in claim 1, wherein the oil-soluble resin is an organo silicone resin comprising the unit, on average:

$R_{11}SiO_{4-n/2}$ wherein R is a hydrocarbon group having 1 to 6 carbon atoms or a phenyl group and n is from 1.0 to 1.8.

3. A water-in-oil type make-up cosmetic composition as claimed in claim 1, wherein the amount of the total oil phase formulated is 40 to 95% by weight and the amount of the total aqueous phase formulated is 5 to 60% by weight.

4. A water-in-oil type make-up cosmetic composition as claimed in claim 1, wherein the aqueous phase contains, in addition to the coloring material, 0.1 to 80% by weight, based on the amount of the aqueous phase, of a film-forming emulsion resin.

5. A water-in-oil type make-up cosmetic composition as claimed in claim 1, wherein the oil phase contains 2 to 50% by weight, based on the oil phase, of oil-soluble resin.

6. A water-in-oil type make-up cosmetic composition as claimed in claim 1, wherein the oil phase contains 5 to 50% by weight, based on the oil phase, of oil-soluble resin.

7. A water-in-oil type make-up cosmetic composition as claimed in claim 1, wherein the cosmetic contains 20 to 60% by weight inner aqueous phase.

8. A water-in-oil type make-up cosmetic composition as claimed in claim 1, wherein the inner aqueous phase contains 0.1–50% coloring material.

* * * * *